US00PP25909P3

(12) United States Plant Patent
Olesen

(10) Patent No.: US PP25,909 P3
(45) Date of Patent: Sep. 22, 2015

(54) MINIATURE ROSE PLANT NAMED 'POULPAH067'

(50) Latin Name: ***Rosa* hybrid**
Varietal Denomination: Poulpah067

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 168 days.

(21) Appl. No.: 13/986,917

(22) Filed: Jun. 14, 2013

(65) Prior Publication Data

US 2014/0373211 P1 Dec. 18, 2014

(51) Int. Cl.
*A01H 5/02* (2006.01)

(52) U.S. Cl.
USPC ..... Plt./118

(58) Field of Classification Search
USPC ..... Plt./101, 116, 118
See application file for complete search history.

(56) References Cited

PUBLICATIONS

UPOV-PLUTO Plant Variety Database, International Union for Protection of New Varieties of Plants, Jan. 19, 2015, obtained for cultiver 'Poulpah067' (1 page total).*
'HelpMeFind' website for roses, clematis and peonies. Cultivar 'Poulpah067'. Retrieved from the Internet http://www.helpmefind.com/rose/pl.php?n=88787 (1 page total).*

* cited by examiner

*Primary Examiner* — Susan McCormick Ewoldt

(57) ABSTRACT

A new miniature rose plant that has abundant, yellow-orange blend flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpah067'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpah067', originated as a single seedling from the stated cross.

The new variety may be distinguished from its male pollen parent and female seed parent primarily by flower coloration and growth habit. The female seed parent is 20 cm in height while the claimed plant is 35 cm in height. The male pollen parent has a general tonality of flower color which is Orange 27 A while the claimed plant is Yellow-Orange Group 16A.

The objective of the hybridization of this rose variety for commercial culture was to create a new and distinct variety with unique qualities, such as:

1. Uniform and abundant yellow-orange blend flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah067' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah067' was selected by the inventor as a single plant from the progeny of the hybridization in 2007.

Asexual reproduction of 'Poulpah067' by cuttings was first done by Mogens N. Olesen in the nursery in Fredensborg, Denmark in 2008. This initial and other subsequent propagations conducted in controlled environments have demonstrated that the characteristics of 'Poulpah067' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah067'.

Specifically illustrated in FIG. 1 are flowers at various stages of development, flower petals, and flowers in parts.

Figure 1:
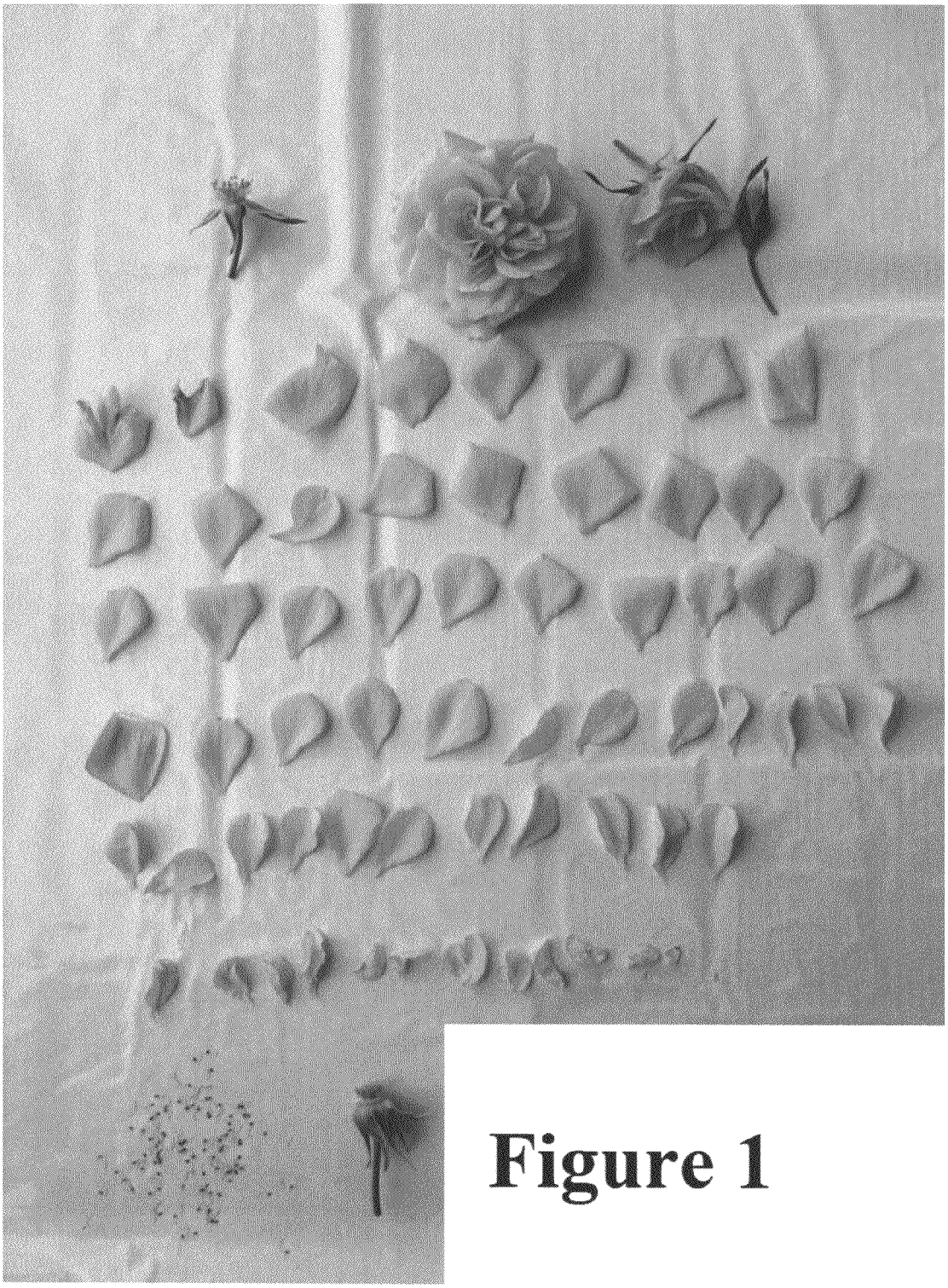
Figure 2:
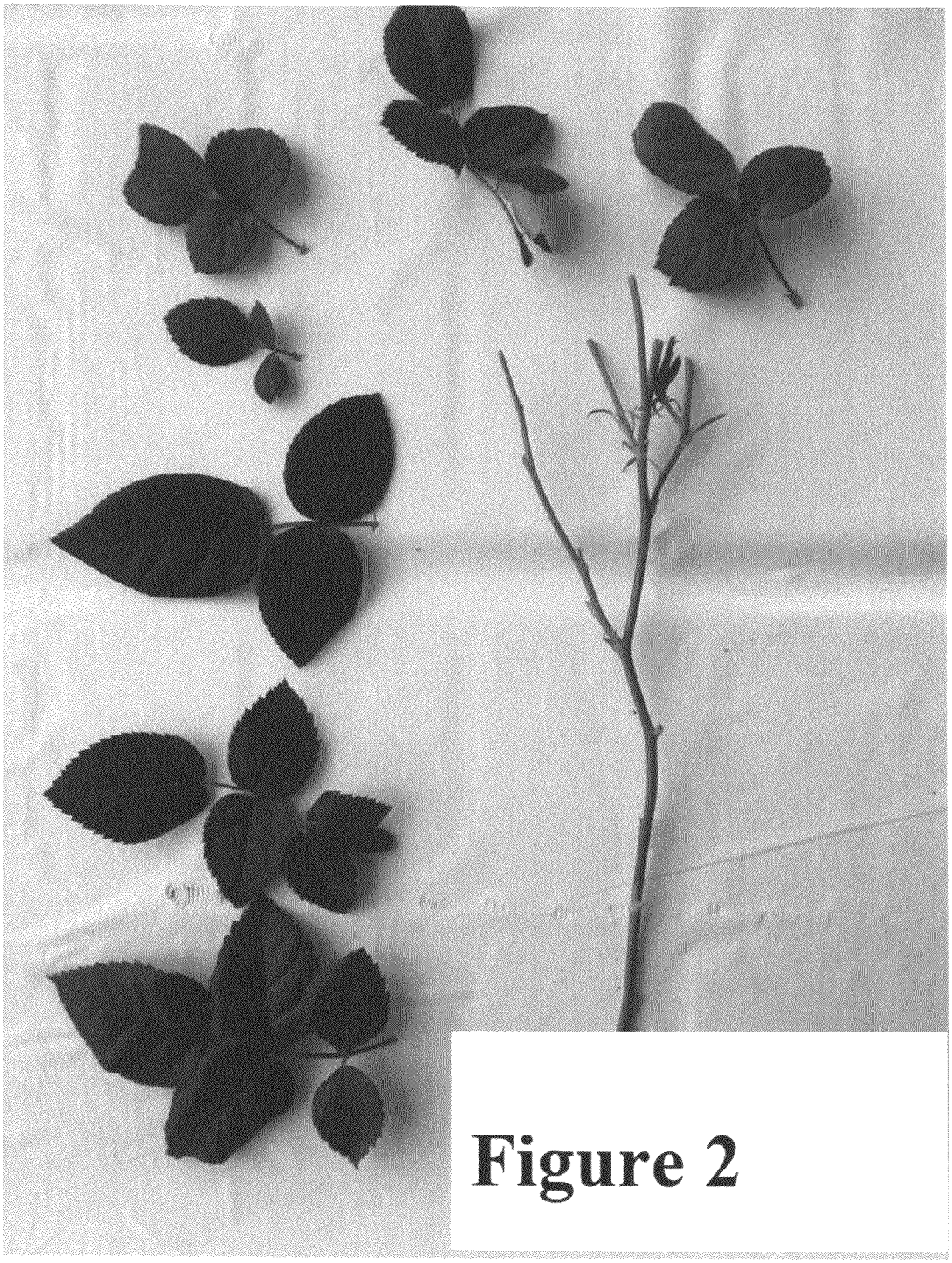

Illustrated in FIG. 2 are leaves, and stems.

Illustrated plants are 5 months of age.

DETAILED DESCRIPTION OF THE VARIETY

The following is a description of 'Poulpah067', as observed in its growth in glasshouses in Fredensborg, Denmark. Observed plants are 5 months of age and were cultivated in 20 cm pots. Color references are made using The Royal Horticultural Society (London, England) Colour Chart, 2001, except where common terms of color are used.

For a comparison, several physical characteristics of the rose variety 'Poulymp', U.S. Plant Pat. No. 16,744 are compared to 'Poulpah067' in Chart 1.

CHART 1

| | 'Poulpah067' | 'Poulymp' |
|---|---|---|
| Petalage: | 62 petals total, 12 of which are petaloids | 25-30 petals under normal conditions with 2-3 petaloids |
| Flower Diameter: | 70 to 80 mm | 60-70 mm |
| General Tonality of Flower Color: | Yellow-Orange Group 16A | Blend Yellow-Orange Group 20B, Orange Group 24C, and Yellow-Orange Group 21C |

FLOWER AND FLOWER BUD

Blooming habit: Continuous.

Flower bud:

*Size.*—Upon opening, 20 mm in length from base of receptacle to end of bud. 12 mm in diameter.

*Bud form.*—Ovate.

*Bud color.*—As sepals unfold, petals are Orange-Red Group 31A.

*Sepals.*—Upper Surface: Color: Yellow-Green Group 147B. Texture: Smooth, moderately pubescent. Lower Surface: Color: Yellow-Green Group 146B. Texture: Smooth. Shape: Apex: Cirrhose. Base: Flat at union with receptacle. Margins: Margins have weak foliaceous appendages on three of the five sepals. Size: 27 mm long by 7 mm wide.

*Receptacle.*—Surface Texture: Smooth. Shape: Campanulate. Size: 5 mm tall and 7 mm wide. Color: Yellow Green Group 144A.

*Pedicel.*—Surface: Smooth. Length: 30 to 65 mm. Diameter: Generally 2 to 3 mm. Color: Yellow-Green Group 144A. Strength: Medium strength.

*Peduncle.*—Length: 6.5 to 14 cm. Diameter: 2 to 3 mm. Color: Yellow-Green Group 144A.

*Borne.*—In corymb form, clustered in groups of 5 to 7 on average.

Flower bloom:

*Fragrance.*—None.

*Duration.*—As a pot plant, flowers last up to 28 days.

*Size.*—Flower diameter is 70 to 80 mm when open. Flower depth is 30 mm.

*Form.*—General shape is a very double rosette, with slightly overlapping petals of different sizes.

*Shape of flower, side view.*—The upper portion is a flattened convex. The lower portion is a flattened concave.

Petalage: Under normal conditions, flowers have 62 petals total, 12 of which are petaloids.

Color:

*General tonality.*—On open flower Yellow-Orange Group 16A.

*Upon opening, petals.*—Outermost and innermost petals are Yellow-Orange Group 18A on the upper surface. Yellow-Orange Group 19A on the lower surface. No distinctive coloration at the petal base observed.

*After opening, petals.*—Outermost and innermost petals are Yellow-Orange Group 18A on the upper surface. Yellow-Orange Group 19A on the lower surface. No distinctive coloration at the petal base observed.

Petals:

*Petal reflex.*—Moderate.

*Margin.*—Entire with weak undulations.

*Shape.*—Generally broad and elliptic and narrow elliptic. Apex shape: Rounded. Base shape: Acute.

*Size.*—35 mm (l) by 40 mm (w).

*Texture.*—Slight texture.

*Thickness.*—Average.

Petaloids:

*Quantity.*—12 on average.

*Shape.*—Irregular, and asymmetric. The apex is rounded and base is acute.

*Color.*—Yellow-Orange Group 18A on the upper surface. Yellow-Orange Group 19A on the lower surface.

*Size.*—15 mm (l) by 8 mm (w).

Reproductive organs:

*Pollen.*—None Observed.

*Anthers.*—Size: 1 mm long. Color: Brown Group 200D. Quantity: 100 on average.

*Filaments.*—Color: Yellow Group 9C. Length: About 5 mm.

*Pistils.*—Length: About 3 mm long. Quantity: 90 on average.

*Stigmas.*—Inferior relative to the length of the filaments and the height of the anthers. Color: Yellow-Orange Group 23A.

*Styles.*—Color: Yellow Group 8A.

*Seed formation.*—Not observed.

PLANT

Plant growth: Upright. Plants are 35 cm in height, and 30 cm wide.

Stems:

*Color.*—Juvenile growth: Yellow-Green Group 144D. Mature growth: Yellow-Green Group 144A.

*Length.*—Canes are 30 cm from the base of the plant to the flowering portion.

*Diameter.*—About 4 mm.

*Internodes.*—On mature canes, there is an average distance of 28 mm between nodes.

*Surface texture.*—Young and mature wood is smooth.

Prickles: None observed.

Plant foliage:

*Compound leaf size.*—115 mm (l) by 75 mm (w) on average.

*Quantity.*—3 to 4 leaves per 10 cm of stem.

*Leaf bearing angle to stem.*—60 degrees.

*Color of juvenile foliage.*—Upper Leaf Surface: Yellow-Green Group 147A. Lower Leaf Surface: Green Group 138B. Anthocyanin: Greyed-Purple Group at the margins.

*Color of mature foliage.*—Upper Leaf Surface: Yellow-Green Group 147A. Lower Leaf Surface: Green Group 138D.

Plant leaves and leaflets:

*Stipules.*—Size: About 7 mm in length. Shape: Linear, slightly broad based with outward extending apecies. Margins: Entire. Color: Yellow-Green Group 144B.

*Petiole*.—Length: 13 mm on average. Diameter: About 1 mm. Upper surface: Yellow-Green Group 144B. Lower surface: Yellow-Green Group 144B.

*Rachis*.—Length: 15 mm on average. Diameter: About 1 mm. Upper surface: Yellow-Green Group 144A. Lower surface: Yellow-Green Group 144B.

*Leaflet*.—Number of leaflets: On normal leaves in middle of the stem there are 5 leaflets. Occasionally 3 and 7 leaflets. Size: 45 mm in length by 34 mm wide. Margin: Serrate. General Shape: Ovate. Apex Shape: Acute. Base Shape: Round. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpah067', substantially as illustrated and described herein, due to its abundant, yellow-orange blend flowers, vigorous growth, compact habit, suitability for production from softwood cuttings in pots, and durable flowers and foliage that make the variety suitable for distribution in the floral industry.

* * * * *